US012657313B2

(12) United States Patent　(10) Patent No.: US 12,657,313 B2
Lee　(45) Date of Patent: Jun. 16, 2026

(54) MEDICAL IMAGE RECONSTRUCTION AND TRANSMISSION SYSTEM AND METHOD

(71) Applicant: AIRS MEDICAL INC., Seoul (KR)

(72) Inventor: Doo Hee Lee, Seoul (KR)

(73) Assignee: AIRS MEDICAL INC., Seoul (KR)

( * ) Notice: Subject to any disclaimer, the term of this patent is extended or adjusted under 35 U.S.C. 154(b) by 550 days.

(21) Appl. No.: 17/424,315

(22) PCT Filed: Jun. 8, 2021

(86) PCT No.: PCT/KR2021/007180
§ 371 (c)(1),
(2) Date: Jul. 20, 2021

(87) PCT Pub. No.: WO2022/203119
PCT Pub. Date: Sep. 29, 2022

(65) Prior Publication Data
US 2023/0153456 A1　May 18, 2023

(30) Foreign Application Priority Data

Mar. 25, 2021　(KR) ........................ 10-2021-0038588

(51) Int. Cl.
*G06F 21/60*　(2013.01)
*G06F 21/62*　(2013.01)
(Continued)

(52) U.S. Cl.
CPC .......... *G06F 21/602* (2013.01); *G06V 10/764* (2022.01); *G06V 10/7715* (2022.01);
(Continued)

(58) Field of Classification Search
USPC ....................................................... 705/2–3
See application file for complete search history.

(56) References Cited

U.S. PATENT DOCUMENTS

2007/0217607 A1* 9/2007 Thiagarajan ............ H03M 7/30
380/217
2011/0110568 A1* 5/2011 Vesper ................... G06Q 10/10
382/128
(Continued)

FOREIGN PATENT DOCUMENTS

KR　　10-1624305 B1　5/2016
KR　　10-1923184 B1　11/2018
(Continued)

OTHER PUBLICATIONS

Huang, Y. (2020). Deep representation and graph learning for disease diagnosis on medical image data (Order No. 29003110). Available from ProQuest Dissertations and Theses Professional. (2637684039). Retrieved from https://dialog.proquest.com/professional/docview/2637684039?accountid=131444 (Year: 2020).*

(Continued)

*Primary Examiner* — Bennett Stephen Erickson
(74) *Attorney, Agent, or Firm* — Harness, Dickey & Pierce, PLC

(57)　　　ABSTRACT

A medical image reconstruction and transmission method employing a medical image reconstruction and transmission system according to an embodiment of the present invention includes receiving medical image data including at least one of k-space data obtained through accelerated imaging and digital imaging and communications in medicine (DICOM) data generated on the basis of the k-space data obtained through accelerated imaging, reconstructing the received medical image data using an artificial neural network model, and transmitting the reconstructed medical image data on the basis of an address from which the medical image data is received.

10 Claims, 7 Drawing Sheets

(51) Int. Cl.

| | |
|---|---|
| *G06V 10/764* | (2022.01) |
| *G06V 10/77* | (2022.01) |
| *G06V 10/82* | (2022.01) |
| *G16H 30/00* | (2018.01) |
| *G16H 30/40* | (2018.01) |
| *H04L 9/40* | (2022.01) |

(52) U.S. Cl.
CPC ............. *G06V 10/82* (2022.01); *G16H 30/00* (2018.01); *G16H 30/40* (2018.01); *H04L 63/0428* (2013.01); *G06F 21/6245* (2013.01)

(56) References Cited

U.S. PATENT DOCUMENTS

| | | | |
|---|---|---|---|
| 2012/0243687 A1* | 9/2012 | Li | H04L 9/085 380/277 |
| 2018/0276852 A1 | 9/2018 | Chen | |
| 2019/0104940 A1* | 4/2019 | Zhou | A61B 5/0035 |
| 2020/0129784 A1* | 4/2020 | Bériault | A61N 5/1048 |
| 2020/0160972 A1* | 5/2020 | Bériault | G06T 7/246 |
| 2020/0202586 A1 | 6/2020 | Li et al. | |
| 2020/0402661 A1* | 12/2020 | Takeshima | G06T 7/0012 |
| 2021/0035290 A1* | 2/2021 | Aben | G06T 7/0012 |
| 2021/0042913 A1* | 2/2021 | Takeshima | G06T 7/0012 |
| 2021/0166445 A1* | 6/2021 | Wang | G06N 3/08 |

FOREIGN PATENT DOCUMENTS

| | | |
|---|---|---|
| KR | 10-2018-0098869 | 5/2019 |
| KR | 10-2019-0138107 A | 12/2019 |
| KR | 10-2020-0044222 A | 4/2020 |
| KR | 10-2097743 B1 | 4/2020 |
| KR | 10-2215702 B1 | 2/2021 |
| WO | 2019/204406 A1 | 10/2019 |

OTHER PUBLICATIONS

Y. Ding et al., "DeepEDN: A Deep-Learning-Based Image Encryption and Decryption Network for Internet of Medical Things," in IEEE Internet of Things Journal, vol. 8, No. 3, pp. 1504-1518, 1 Feb. 1, 2021, doi: 10.1109/JIOT.2020.3012452. (Year: 2021).*

Ran, M., et al., "MD-Recon-Net: A Parallel Dual-Domain Convolutional Neural Network for Compressed Sensing MRI", IEEE Transactions on Radiation and Plasma Medican Sciences, vol. 5, No. 1, Jan. 2021, pp. 1-16.

Zhou, Z., et al.; "Parallel imaging and convolutional neural network combined fast MR imagine reconstruction: Applications in low-latency accelerated real-time imaging", Med. Phys., 46, 8, Aug. 2019, pp. 1-15.

International Search Report from corresponding PCT Application No. PCT/KR2021/007180, dated Dec. 21, 2021.

Written Opinion from the International Searching Authority from corresponding PCT Application No. PCT/KR2021/007180, dated Dec. 21, 2021.

Cho, Y., et al.; "AES Encryption Algorithm for safe PACS data Transmission in the Cloud Environment", Science ON, 2017, pp. 759-762.

Extended European Search Report from corresponding EP Application No. 21933347.3, dated Feb. 26, 2025.

* cited by examiner

MEDICAL IMAGE RECONSTRUCTION AND TRANSMISSION SYSTEM AND METHOD

CROSS-REFERENCE TO RELATED APPLICATIONS

This application is a national phase application of PCT Application No. PCT/KR2021/007180, filed on 8 Jun. 2021, which claims the benefit of and priority to Korean Patent Application No. 10-2021-0038588, filed on 25 Mar. 2021. The entire disclosures of the applications identified in this paragraph are incorporated herein by references.

TECHNICAL FIELD

The present invention relates to a medical image reconstruction and transmission system and method for reconstructing a medical image using artificial intelligence and transmitting the medical image by performing encryption and decryption.

BACKGROUND

In hospitals, a digital picture archiving and communication system (PACS) is generally used to acquire and store medical images captured by X-ray, computed tomography (CT), magnetic resonance imaging (MRI), or ultrasound equipment, which is medical imaging and diagnostic equipment, as digital data and processing functions required for transmitting the interpretation and the medical record together to each terminal and searching for the interpretation and the medical record in an integrated manner. The PACS stores and manages medical images according to digital imaging and communications in medicine (DICOM) which is an industry standard communication protocol for transmitting medical images and information between different types of medical imaging devices.

Also, the PACS makes it possible to process existing hospital work of diagnosis and interpretation based on film through a computer and a network so that hospital work may be efficiently carried out.

Meanwhile, with the advance of artificial intelligence, technologies are being developed to train artificial intelligence, such as a deep learning algorithm, with massive medical image data and to use the artificial intelligence in making a medical determination.

However, medical image data used in PACS can neither be directly used in training a deep learning algorithm nor directly applied to reconstruction and processing with a deep learning algorithm. Accordingly, it is necessary to develop a system capable of pre-processing and post-processing medical image data.

Also, since there are security-sensitive issues, such as personal information and body images contained in medical image data, encryption, such as pseudonymization, of medial image data is required for transmission and reception of the medical image data between a PACS server and an external server which provides a deep learning algorithm.

SUMMARY

Technical Problem

The present invention is directed to providing a medical image reconstruction and transmission method for encrypting medical image data, which includes personal information and is transmitted and received between a medical institute and a medical image reconstruction and transmission system, through pseudonymization to provide enhanced security and prevent leakage of the personal information.

The present invention is also directed to providing a medical image reconstruction and transmission method which reconstructs a medical image using an optimal artificial neural network model according to feature information of medical image data to acquire the medical image of improved quality.

Technical Solution

One aspect of the present invention provides a medical image reconstruction and transmission method using a medical image reconstruction and transmission system, the method including receiving medical image data including at least one of k-space data obtained through accelerated imaging and digital imaging and communications in medicine (DICOM) data generated on the basis of the k-space data obtained through accelerated imaging, reconstructing the received medical image data using an artificial neural network model, and transmitting the reconstructed medical image data on the basis of an address from which the medical image data is received.

The medical image reconstruction and transmission method may further include encrypting the medical image data before the reconstructing of the medical image data using the artificial neural network model.

The encrypting of the medical image data may include shuffling a plurality of image slices included in the medical image data.

The medical image reconstruction and transmission method may further include storing the encrypted medical image data and deleting the unencrypted medical image data.

The medical image reconstruction and transmission method may further include decrypting the stored encrypted medical image data and reconstructing the decrypted medical image data using the artificial neural network model.

The medical image reconstruction and transmission method may further include classifying the medical image data according to feature information of the medical image data and transmitting the medical image data classified according to the feature information to the artificial neural network model so that the classified medical image data may be input in a distributed manner to a plurality of artificial neural network models classified in advance on the basis of the feature information.

The feature information may include at least one of protocol information and sequence information of the medical image data.

The medical image reconstruction and transmission method may further include, when the feature information includes both the protocol information and the sequence information, generating a protocol image set from the medical image data on the basis of the protocol information, classifying a plurality of medical images included in the protocol image set into the sequence information, generating a sequence image set on the basis of the classified sequence information, and transmitting the sequence set to the artificial neural network model.

Another aspect of the present invention provides a medical image reconstruction and transmission system which receives medical image data including at least one of k-space data obtained through accelerated imaging and DICOM data generated on the basis of the k-space data obtained through accelerated imaging, reconstructs the received medical image data using an artificial neural network model, and transmits the reconstructed medical image data on the basis of an address from which the medical image data is received.

Encryption may be performed on the medical image data before the medical image data is reconstructed using the artificial neural network model.

The encryption may include shuffling a plurality of image slices included in the medical image data.

The medical image reconstruction and transmission system may store the encrypted medical image data and delete the unencrypted medical image data.

The medical image reconstruction and transmission system may decrypt the stored encrypted medical image data and reconstruct the decrypted medical image data using the artificial neural network model.

The medical image reconstruction and transmission system may classify the medical image data according to feature information of the medical image data and transmit the medical image data classified according to the feature information to the artificial neural network model so that the classified medical image data may be input in a distributed manner to a plurality of artificial neural network models classified in advance on the basis of the feature information.

The feature information may include at least one of protocol information and sequence information of the medical image data.

When the feature information includes both the protocol information and the sequence information, the medical image reconstruction and transmission system may generate a protocol image set from the medical image data on the basis of the protocol information, classify a plurality of medical images included in the protocol image set into the sequence information, generate a sequence image set on the basis of the classified sequence information, and transmit the sequence set to the artificial neural network model.

Advantageous Effects

A medical image reconstruction and transmission method according to an embodiment of the present invention provides enhanced security by encrypting medical image data, which includes personal information and is transmitted and received between a medical institute and a medical image reconstruction and transmission system, through pseudonymization, and thus it is possible to prevent leakage of the personal information.

The medical image reconstruction and transmission method according to an embodiment of the present invention reconstructs a medical image using an optimal artificial neural network model according to feature information of the medical image data, and thus it is possible to acquire a medical image of improved quality.

DETAILED DESCRIPTION

Figure 1:
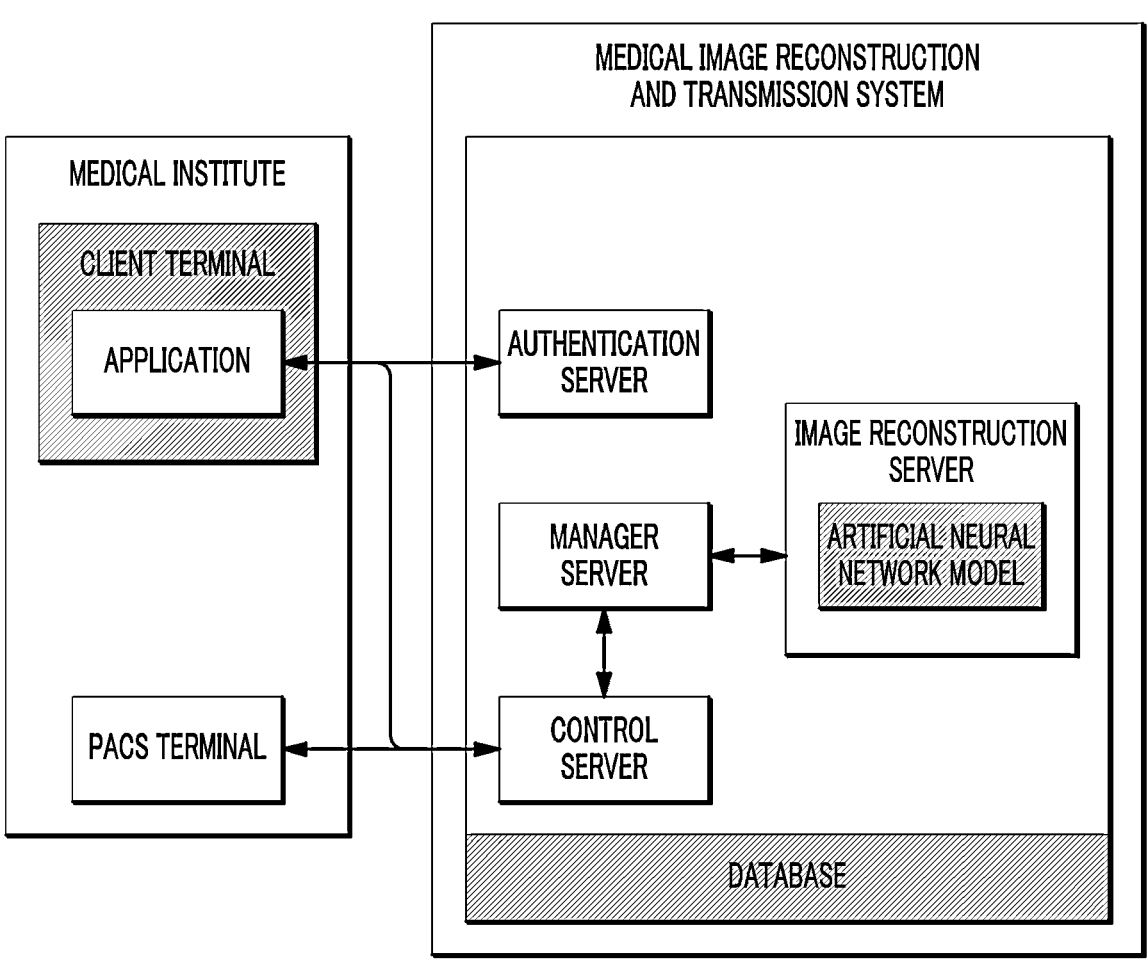
FIG. 1 is a diagram illustrating a configuration of a medical image reconstruction and transmission system according to an embodiment of the present invention.

Hereinafter, embodiments of the present invention will be described in detail with reference to the accompanying drawings so that those of ordinary skill in the art can readily implement the present invention. However, the present invention can be implemented in various different forms and is not limited to the embodiments disclosed herein. To clearly describe the present invention, parts irrelevant to the description are omitted in the drawings. Throughout the drawings, like elements are noted by like reference numerals.

Throughout the specification, when a part is referred to as being "connected" to another part, this includes not only being "directly connected" but also being "electrically connected" by interposing another element therebetween. Also, when a part "includes" an element, it is noted that the part may further include other elements and does not exclude other elements unless specifically stated otherwise.

In this specification, a "server" and a "system" mean a computer which includes one or more memories (not shown), one or more computer processors (not shown), and one or more programs (not shown). Here, the one or more programs (hereinafter, "pre-processing programs") may be stored in the memory and executed by the one or more processors, and the one or more memories, the one or more computer processors, and the one or more programs may be physically located in the same device and directly connected or may be connected via a communication network.

In this specification, an "image" may mean multi-dimensional data including discrete image elements (e.g., pixels in a two-dimensional image and VOlume piXELs (VOXELs) in a three-dimensional image). For example, an image may include a medical image acquired by medical imaging equipment such as magnetic resonance imaging (MRI) equipment, computed tomography (CT) equipment, ultrasonic imaging equipment, or X-ray imaging equipment.

In this specification, "image reconstruction" may include increasing the resolution of a low-resolution image, increasing the signal-to-noise ratio (SNR) of an image, or reducing aliasing patterns or artifacts or may mean improving the quality of a low-quality image. Also, MRI does not only have the above-described meaning "image construction" but may also mean processing an image generated from subsampled k-space data to be identical or similar to an image generated from full-sampled k-space data.

A medical image reconstruction and transmission system according to an embodiment of the present invention will be described in detail below with reference to the accompanying drawings.

FIG. 1 is a diagram illustrating a configuration of a medical image reconstruction and transmission system according to an embodiment of the present invention.

Referring to FIG. 1, the medical image reconstruction and transmission system according to the embodiment of the present invention transmits and receives medical image data by communicating with a picture archiving and communication system (PACS) used in a medical institute and reconstructs medical image data using an artificial neural network model.

The medical image reconstruction and transmission system according to the embodiment of the present invention may be implemented in the form of a cloud computing system. Cloud computing means a computing environment in which it is possible to use information technology (IT)-related services, such as data storage, network, and content use, through a server on the Internet in an integrated manner. Unlike this, the medical image reconstruction and transmission system may be implemented in various forms of computing systems capable of performing a medical image reconstruction and transmission method such as server computing, edge computing, and serverless computing.

The medical image reconstruction and transmission system according to the embodiment of the present invention may include a communication module, a memory, and a processor.

The communication module interoperates with a communication network to provide a communication interface to the medical image reconstruction and transmission system and may serve to transmit or receive data to or from a client terminal, a PACS terminal, and a PACS server which will be described below. Here, the communication module may be a device including hardware and software required for transmitting or receiving a signal, such as a control signal or a data signal, to or from another network device through a wired or wireless connection.

Meanwhile, in the present invention, a "terminal" may be a wireless communication device with ensured portability and mobility and may be any type of handheld wireless communication device, for example, a smart phone, a tablet personal computer (PC), and a laptop computer. Also, a "terminal" may be a wearable device, such as a watch, glasses, a hairband, and a ring, having a communication function and a data processing function. In addition, a "terminal" can be a wired communication device, such as a PC, capable of accessing another terminal, a server, or the like via a network.

The memory may be a storage medium in which a program executed in the medical image reconstruction and transmission system is recorded. Also, the memory may perform a function of storing data processed by the processor temporarily or permanently. Here, the memory may include volatile storage media or non-volatile storage media, but the scope of the present invention is not limited thereto.

The processor may control the overall process of the program executed in the medical image reconstruction and transmission system. Here, the processor may include any type of device capable of processing data as a processor. The "processor" may denote a data processing device which is embedded in hardware and has a physically structured circuit to perform a function represented as a code or command included in the program. Examples of the data processing device embedded in hardware as described above may include processing devices, such as a microprocessor, a central processing unit (CPU), a processor core, a multiprocessor, an application-specific integrated circuit (ASIC), a field programmable gate array (FPGA), and a graphics processing unit (GPU), but the scope of the present invention is not limited thereto.

The medical image reconstruction and transmission system according to the embodiment may include a control server, a manager server, an image reconstruction server, and an authentication server. When the medical image reconstruction and transmission system is implemented as a cloud computing system, the medical image reconstruction and transmission system may include a virtual control server, manager server, image reconstruction server, and authentication server on the Internet, which may be included in a single cloud server. For example, in the single cloud server, the virtual control server, manager server, image reconstruction server, and authentication server have different Internet protocol (IP) addresses, and on the basis of the different IP addresses, data may be transmitted, and each function may be performed. Alternatively, all of the control server, manager server, image reconstruction server, and authentication server may have the same IP address, and the medical image reconstruction and transmission method may be performed through data transmission according to a preset algorithm.

Meanwhile, in a medical institute, a client terminal which interoperates with a medical image imaging apparatus to control the imaging apparatus or manage transmission of medical image data and a PACS terminal on which a PACS program enabling a medical worker to see or process and manage medical image data may be generally disposed.

The client terminal may be a terminal on which a program that provides a user interface (UI) for outputting record of user login, a worklist, and image processing is installed. The PACS terminal may be a terminal on which a program providing a UI for transmitting medical image data and personal information data stored in the PACS server to the control server of the medical image reconstruction and transmission system, receiving medical image data reconstructed through the image reconstruction server, and transmitting the medical image data in the PACS server is installed.

The control server of the medical image reconstruction and transmission system may perform a function of transmitting or receiving medical image data to or from the PACS terminal and the PACS server and provide a worklist and image processing information application programming interface (API).

The manager server may receive medical image data from the control server and automatically assign an image processing task to the image reconstruction server so that the image reconstruction server may rapidly reconstruct an image.

The image reconstruction server may receive the medical image data from the manager server and reconstruct the received medical image data using the artificial neural network model and the GPU. The artificial neural network model may be a deep learning model which is trained in advance for image quality improvement processing. The artificial neural network model will be described in detail below.

The authentication server may provide a user authentication and management API for using a program of the medical image reconstruction and transmission method.

In a database, various pieces of data required for the medical image reconstruction and transmission system to execute the program may be stored. For example, a user list, a worklist, image processing information and protocol rules, and medical image data may be stored in the database.

Figure 2:
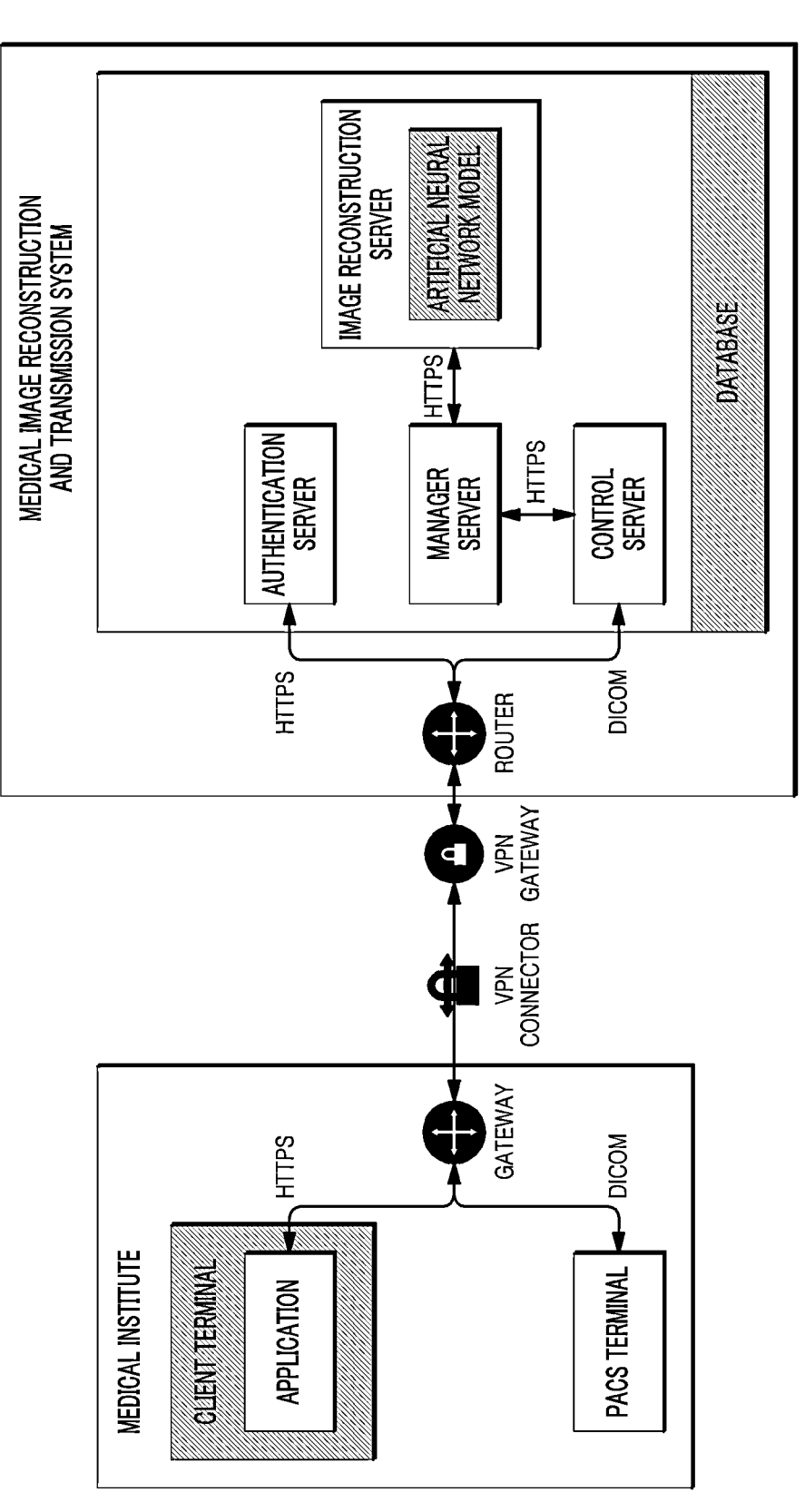
FIG. 2 is a diagram illustrating network communication between a medical image reconstruction and transmission system and a picture archiving and communication system (PACS) according to an embodiment of the present invention.

FIG. 2 is a diagram illustrating network communication between a medical image reconstruction and transmission system and a PACS according to an embodiment of the present invention.

Referring to FIG. 2, a PACS server and a medical image reconstruction and transmission system may communicate with each other using an encrypted wired network on the basis of a site-to-site virtual private network (VPN). Three elements, user authentication, data integrity, and data confidentiality, are required for a network tunnel to completely protect data. Such a secure tunnel is referred to as a VPN. In particular, site-to-site VPN may establish an encrypted tunnel between networks in different sites, and data and resources may be safely shared between the sites via the Internet.

Specifically, a client terminal may perform VPN communication with an authentication server to transmit or receive the encrypted information of login information, personal information, and medical image data through hypertext transfer protocol secure (HTTPS). HTTPS is a secure version of HTTP which is a World Wide Web communication protocol. A PACS terminal may perform VPN communication with a control server to transmit or receive digital imaging and communications in medicine (DICOM) data which is encrypted medical image data.

A medical image reconstruction and transmission method employing the medical image reconstruction and transmission system will be described in detail below according to an embodiment of the present invention.

Figure 3:
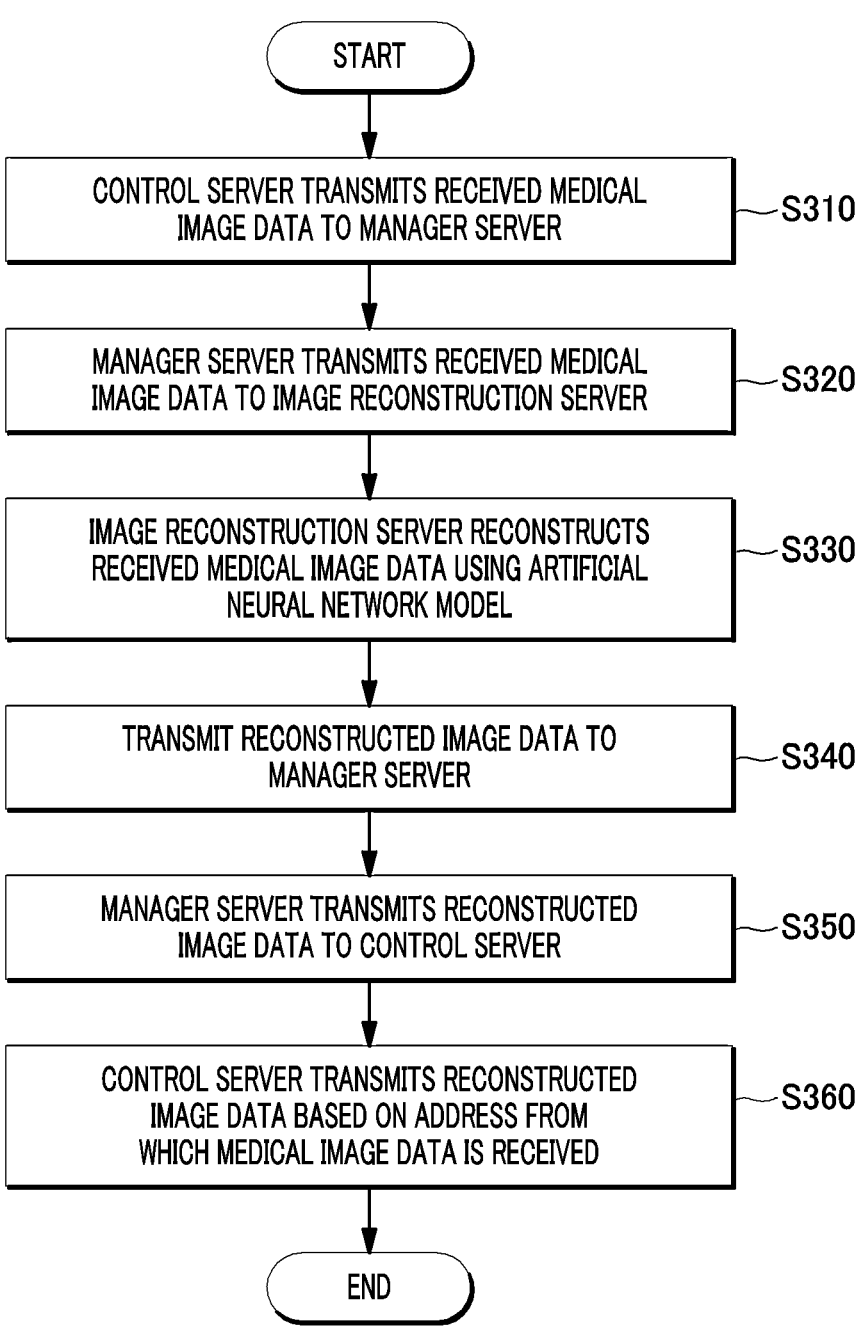
FIG. 3 is a flowchart illustrating a medical image reconstruction and transmission method performed using a medical image reconstruction and transmission system according to an embodiment of the present invention.

FIG. 3 is a flowchart illustrating a medical image reconstruction and transmission method performed using a medical image reconstruction and transmission system according to an embodiment of the present invention.

Referring to FIG. 3, in the medical image reconstruction and transmission method according to the embodiment of the present invention, an operation S310 may be performed in which a control server transmits received medical image data to a manager server.

The medical image data may include at least one of k-space data obtained through accelerated imaging and DICOM data generated on the basis of the k-space data obtained through accelerated imaging.

Accelerated imaging may mean shortening the imaging time by reducing the number of excitations (NEX) when medical image data corresponds to images obtained through MRI. For example, accelerated imaging may mean imaging a sequence, which is generally imaged two times in a repeated manner, once. Also, accelerated imaging may mean obtaining a low-resolution image by obtaining a signal having a narrower range in a phase-encoding direction in the k-space. Further, when medical image data corresponds to images obtained through MRI, accelerated imaging may mean acquiring subsampled magnetic resonance signals by shortening the MRI time. The subsampled magnetic resonance signals may be magnetic resonance signals sampled at a sampling rate lower than the Nyquist sampling rate. In other words, a magnetic resonance image obtained through accelerated imaging may be an image acquired by sampling magnetic resonance signals at a sampling rate lower than the Nyquist sampling rate. A subsampled magnetic resonance image may be an image including artifacts which are various artificial images.

For example, a full-sampled magnetic resonance signal may have n lines, and a subsampled magnetic resonance signal may have n/2 lines. Here, when a reduction in the number of sampling lines is a multiple of ½, an MRI acceleration index may be 2. When reductions in the number of sampling lines are a multiple of ⅓ and a multiple of ¼, MRI acceleration indices may be 3 and 4, respectively. In addition, accelerated imaging may be an imaging method obtained by combining one or more of the above-described imaging methods.

The control server may receive the medical image data including at least one of the k-space data obtained through accelerated imaging and the DICOM data generated on the basis of the k-space data obtained through accelerated imaging from medical imaging equipment and the PACS.

The medical image data may include vital information of a patient, medical image information, which is a still image of the patient, an area under treatment, or the like generated in the medical field, and medical moving image or medical video information captured in the medical field.

DICOM denotes a digital image and communication standard for medical purposes and collectively refers to several standards used for digital image representation and communication in medical equipment.

The DICOM data may mainly include patient information and media characteristics. For example, various pieces of medical information data included in the DICOM data is patient-related text information collected from the medical field and unprocessed media information, and there are no restrictions on the format of the medical information data. More specifically, the DICOM data may include vital information of the patient, medical image information, which is a still image of the patient, the area under treatment, or the like generated in the medical field, and medical moving image or medical video information captured in the medical field.

Figure 4A:
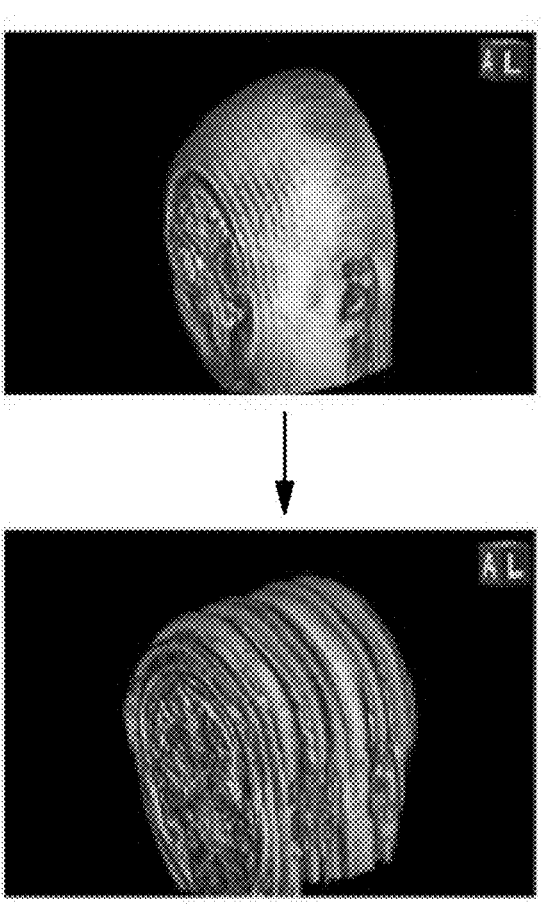
FIG. 4A, 4B, 4C are sets of views illustrating a medical image data encryption method according to an embodiment of the present invention.
Figure 4B:
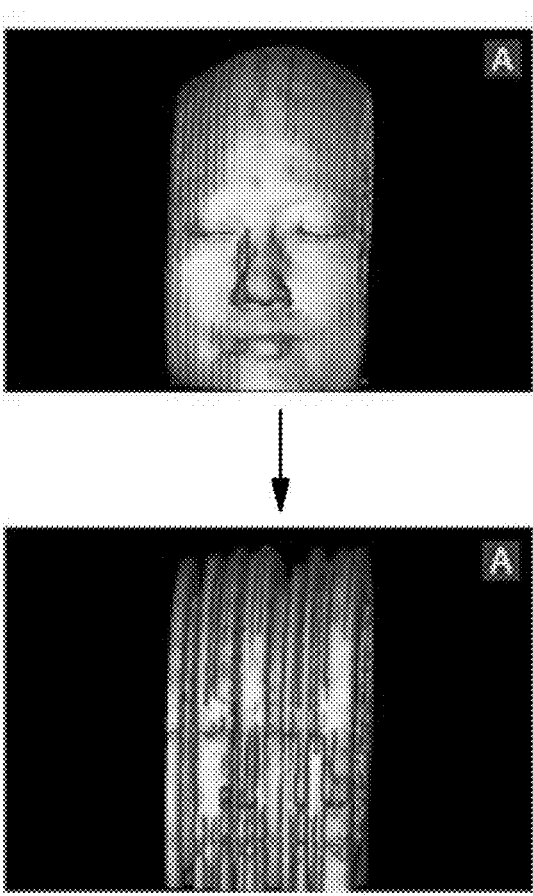
Figure 4C:
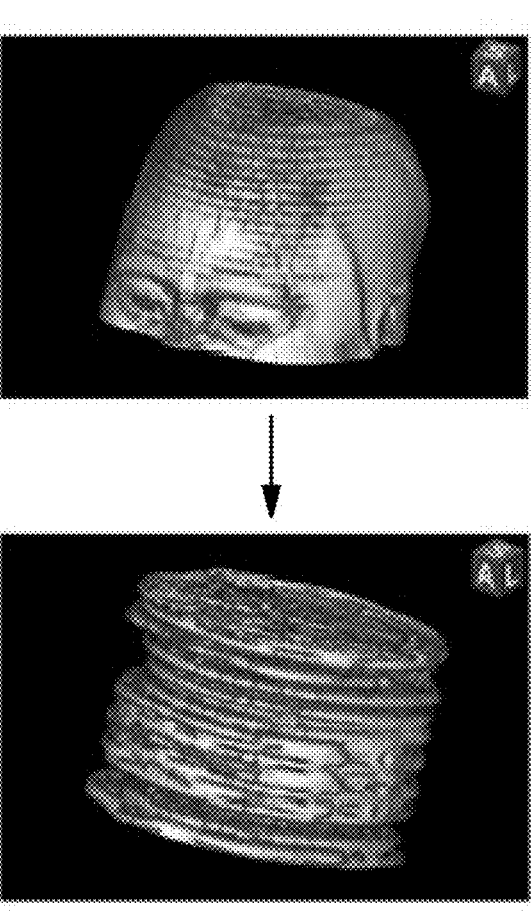

FIG. 4A, 4B, 4C are sets of views illustrating a medical image data encryption method according to an embodiment of the present invention.

Referring to FIG. 4A, 4B, 4C the control server may encrypt medical image data before transmitting the medical image data to the manager server. Encrypting the medical image data may include shuffling a plurality of image slices included in the medical image data.

Here, "encryption" may include anonymization. Specifically, anonymization may be deleting or converting all or some of included personal identification information into an unrecognizable form. As anonymization techniques, there are various methods including pseudonym, generalization, permutation, perturbation, and the like.

For example, a medical image may be a three-dimensional (3D) image formed by accumulating a plurality of image slices. Also, a plurality of image slices may be generated by slicing such a 3D image in each direction. Shuffling the image slices may be arbitrarily mixing and arranging the sequenced image slices. The 3D medical image makes it possible to detect the face or head shape of the patient and recognize which patient corresponds to the image, and thus there is a risk that personal information may be leaked. To prevent this risk, the medical image reconstruction and transmission system shuffles medical images received from a medical institute and performs pseudonymization of replacing personal information of data with a pseudonym by blinding or deleting metadata, such as personal information, included in medical image data for encryption.

For example, a 3D image of a patient's head shape may be formed by separately stacking coronal, sagittal, and axial image slices. A coronal plane is a cross section obtained by cutting the head in a vertical direction parallel to the face while looking at the face from the front, and coronal image slices may be stacked to form a 3D head image. Pseudonymization of the 3D image may be performed by changing the sequence of stacking the coronal slices for encryption (see FIG. 4A). A sagittal plane is a cross section obtained by cutting the head in a vertical direction parallel to a side surface of the face while looking at the face from the side surface. The sagittal image slices may be stacked to form a 3D head image. Pseudonymization of the 3D image may be performed by changing the sequence of stacking the sagittal slices for encryption (see FIG. 4B). An axial plane is a cross section which divides the head into an upper portion and a lower portion. Axial image slices may be stacked to form a 3D head image. Pseudonymization of the 3D image may be performed by changing the sequence of stacking the slices for encryption (see FIG. 4C).

The control server may store encrypted medical image data and delete unencrypted medical image data to prevent leakage of personal information. When a request for image reconstruction is received, the control server may decrypt encrypted medical image data stored in advance and transmit the decrypted medical image data to the manager server. The control server may classify the medical image data according to feature information of the medical image data and transmit the medical image data to the manager server. The feature information may include at least one of protocol information and sequence information of the medical image data.

Protocol information is information on a combination of various sequences designed to optimally evaluate an image according to an imaged area or lesion in medical imaging. Sequence information is information for creating a specific image shape. In the case of MRI, sequence information includes specific settings for a pulse sequence and pulse field gradation. For example, multiparametric MRI may involve a combination of two or more sequences and/or other special MRI elements such as a spectroscope.

When the feature information includes both protocol information and sequence information, the control server may generate a protocol image set from the received medical image data on the basis of the protocol information. Then, the control server may classify a plurality of medical images included in the protocol image set into the sequence information, generate a sequence image set on the basis of the classified sequence information, and transmit the generated sequence image set to the manager server.

Subsequently, an operation S320 may be performed in which the manager server transmits the received medical image data to the image reconstruction server.

The manager server may transmit the medical image data classified according to the feature information to the image reconstruction server so that the medical image data may be input to a plurality of artificial neural networks of the image reconstruction server, which are classified in advance on the basis of the feature information, in a distributed manner. For example, the manager server may transmit the above-described sequence image set to each of the artificial neural network models stored in the image reconstruction server.

Subsequently, an operation S330 may be performed in which the image reconstruction server reconstructs the received medical image data using the artificial neural network model.

The artificial neural network model may be a set of algorithms for learning the relationship between at least one subsampled magnetic resonance image and at least one full-sampled magnetic resonance image using statistical machine learning results. The artificial neural network model may include at least one neural network. The neural network may include network models such as a deep neural network (DNN), a recurrent neural network (RNN), a bidirectional recurrent deep neural network (BRDNN), a multilayer perceptron (MLP), and a convolutional neural network (CNN), but the artificial neural network is not limited thereto.

For example, the artificial neural network model may be a model built by learning the relationship between at least one subsampled magnetic resonance image and at least one full-sampled magnetic resonance image through a neural network in units of pixels of at least one sampling line stacked in a phase encoding direction. Also, the artificial neural network model may be built with various pieces of additional data in addition to a subsampled magnetic resonance image and a full-sampled magnetic resonance image. For example, at least one of k-space data, real number image data, imaginary number image data, size image data, phase image data, multichannel radio frequency (RF) coil sensitivity data, and noise pattern image data corresponding to the magnetic resonance image may be used as the additional data.

Figure 5:
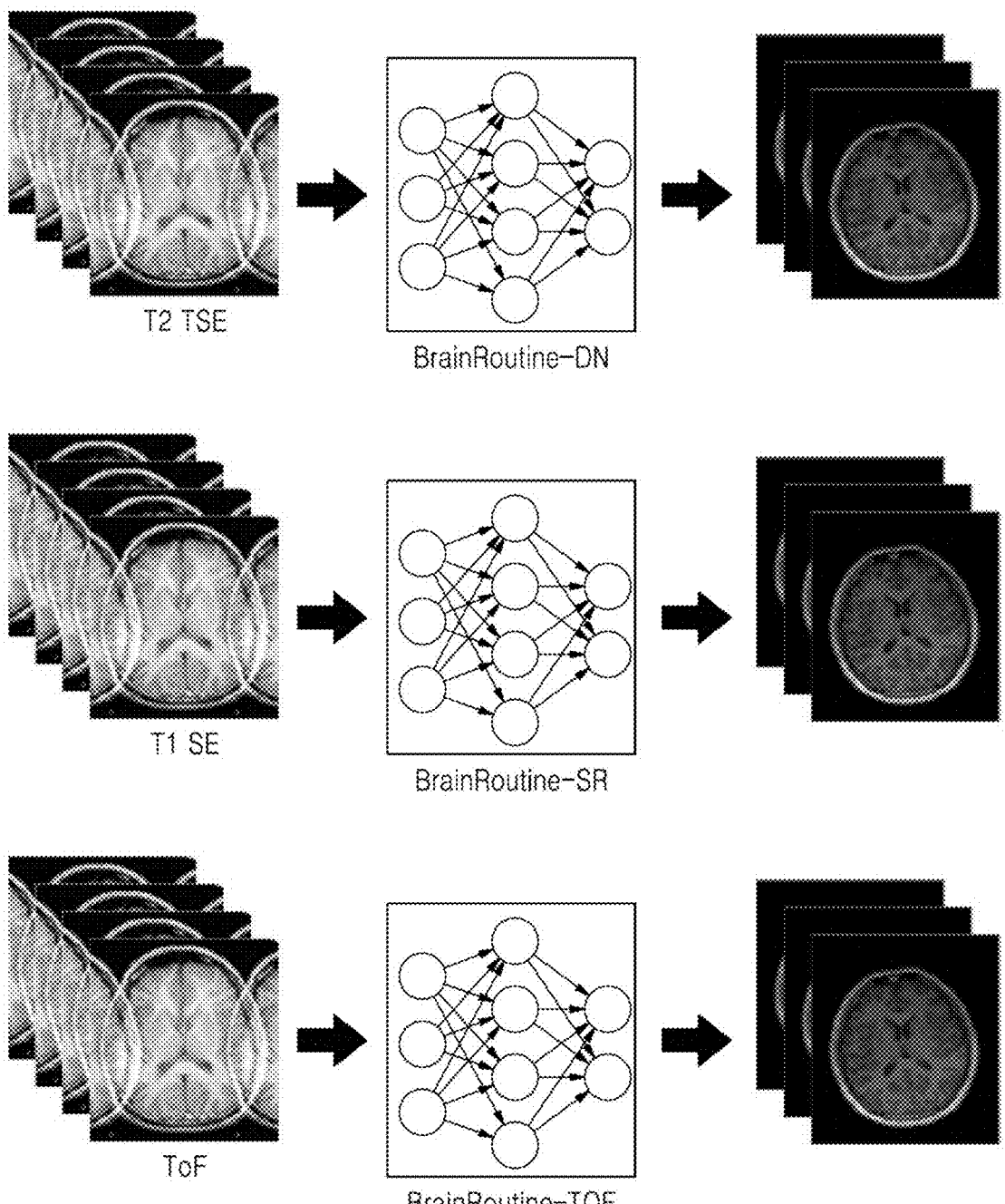
FIG. 5 is a set of views illustrating that an artificial neural network model being applied varies depending on feature information of medical image data according to an embodiment of the present invention.

FIG. 5 is a set of views illustrating that an artificial neural network model being applied varies depending on feature information of medical image data according to an embodiment of the present invention.

Referring to FIG. 5, when an artificial neural network model reconstructs MRI DICOM medical image data, information on a protocol of the medical image data may be, for example, Brain Routine-denoising (DN), and the protocol may include sequences such as T2 turbo-spin echo (TSE), T2 fluid-attenuated inversion recovery (FLAIR), T1 FLAIR, and the like. Accelerated medical imaging according to this sequence is characterized by noise amplified in the image as a result. Accordingly, an artificial neural network model specialized in reducing noise may be applied as an artificial neural network model matching this sequence.

Also, the protocol may be Brain Routine-super resolution (SR), and this protocol may include a sequence such as T1 spin echo (SE) and the like. Accelerated medical imaging according to this sequence is characterized by the resolution of the image reduced as a result. Accordingly, an artificial neural network model specialized in preventing a reduction in resolution may be applied as an artificial neural network model matching this sequence.

The protocol may be Brain Routine-time of flight (TOF), and this protocol may include a sequence such as ToF and the like. This sequence is a 3D imaging sequence and thus may utilize slice direction information. This sequence requires an additional post-processing operation as a result. Accordingly, an artificial neural network model for reading 3D slice direction information and performing a 3D data post-processing operation may be applied as an artificial neural network model matching this sequence.

Subsequently, an operation S340 of transmitting the reconstructed image data to the manager server may be performed. For example, the manager server may receive a plurality of medical images formed as a protocol set and/or a sequence set.

Subsequently, an operation S350 may be performed in which the manager server transmits the received reconstructed image data to the control server. Then, an operation S360 may be performed in which the control server transmits the reconstructed image data on the basis of an address from which the control server receives the medical image data. For example, when the medical image data is received from the PACS server, the control server may transmit the reconstructed image data to the PACS server. The PACS server may encrypt the received reconstructed image data. In this way, the PACS server and the medical image reconstruction and transmission system transmit and receive medical image data using a single tunnel, and thus it is possible to provide a strong security communication system which prevents leakage of a patient's personal information and the like.

With the above-described medical image reconstruction and transmission method according to the embodiment of the present invention, medical image data, which includes personal information and is transmitted and received between a medical institute and a medical image reconstruction and transmission system, is encrypted through pseudonymization to provide enhanced security, and thus it is possible to prevent leakage of the personal information.

With the medical image reconstruction and transmission method according to the embodiment of the present invention, a medical image is reconstructed using an optimal artificial neural network model according to feature information of medical image data, and thus it is possible to acquire the medical image of improved quality.

Meanwhile, the medical image reconstruction and transmission method according to the embodiment may be implemented in the form of a recording medium including computer-executable instructions such as a program module executed by a computer. Computer-readable media may be any available media accessible by a computer and include both volatile and non-volatile media and both removable and non-removable media. Also, the computer-readable media may include computer storage media. Computer storage media include both volatile and non-volatile media and both removable and non-removable media implemented in any method or technology for storage of information such as computer-readable instructions, data structures, program modules, or other data. Although the method and system of the present invention have been described in connection with specific embodiments, some or all of the elements or operations may be implemented using a computer system having a general-purpose hardware architecture.

The above description is merely illustrating the technical spirit of the present invention, and those of ordinary skill in the art would be able to make various modifications and alterations without departing from essential features of the present invention. Therefore, the embodiments disclosed in the present invention are intended not to limit but to illustrate the technical spirit of the present invention, and the technical scope of the present invention is not limited by the embodiments. The scope of the present invention should be construed on the basis of the following claims, and all the technical spirits within the scope equivalent to the claims should be construed as falling into the scope of the present invention.

What is claimed is:

1. A magnetic resonance (MR) image reconstruction and transmission method using a MR image reconstruction and transmission system communicating with a picture archiving and communication system (PACS) through an encrypted wired network, the method comprising:

receiving MR image data including a plurality of k-space data obtained by sub-sampling through accelerated imaging using a MR device and digital imaging and communications in medicine (DICOM) data generated based on the k-space data from the PACS, by a control server of the MR image reconstruction and transmission system;

encrypting the MR image data and storing the encrypted MR image data by the control server;

reconstructing the received MR image data using an artificial neural network model trained to learn a correlation between sub-sampled MR images and fully-sampled MR images based on feature information of the MR image data by a reconstruction server of the MR image reconstruction and transmission system; and transmitting the reconstructed MR image data on the basis of an address from which the MR image data is received to the PACS by the control server,

wherein the encrypting of the MR image data comprises:

obtaining metadata including personal information from the MR image data, and a plurality of image slices by slicing a 3D image included in the MR image data; and encrypting the plurality of image slices by shuffling the plurality of image slices and encrypting the metadata by performing pseudonymization by replacing personal identification information within the metadata, and wherein the encrypting of the plurality of image slices by shuffling the plurality of image slices comprises, rearranging a spatial stacking order of the plurality of image slices with respect to at least one plane among a coronal plane, a sagittal plane, and an axial plane, which constitute the MR image data, and wherein reconstructing the received MR image data comprises:

decrypting the stored encrypted MR image data;

transmitting the decrypted MR image data to a manager server of the MR image reconstruction and transmission system by the control server when a request for the MR image reconstruction is received;

identifying protocol information and sequence information included in the feature information by the manager server and identifying the artificial neural network model corresponding to the protocol information and the sequence information among a plurality of artificial neural network models by the manager server, wherein the protocol information and the sequence information being set in the MR device for the accelerated imaging; and transmitting the decrypted MR image data to the reconstruction server corresponding to the identified artificial neural network model, and reconstructing the decrypted MR image data by inputting the received MR image data into the identified artificial neural network model by the reconstruction server, wherein the protocol information is information set in the MR device corresponding to an anatomical region and lesion to be imaged by the MR device, and wherein the sequence information is information comprising a combination of a plurality of sequences set in the MR device for the accelerated imaging, the combination defining the protocol information.

2. The MR image reconstruction and transmission method of claim 1, further comprising storing the encrypted MR image data and deleting unencrypted MR image data.

3. The MR image reconstruction and transmission method of claim 1, further comprising classifying the MR image data according to feature information of the MR image data and transmitting the MR image data classified according to the feature information to the artificial neural network model so that the classified MR image data is input in a distributed manner to the plurality of artificial neural network models classified in advance on the basis of the feature information.

4. The MR image reconstruction and transmission method of claim 3, further comprising, when the feature information includes both the protocol information and the sequence information, generating a protocol image set from the MR image data on the basis of the protocol information, classifying a plurality of MR images included in the protocol image set into the sequence information, generating a sequence image set on the basis of the classified sequence information, and transmitting a sequence set to the artificial neural network model.

5. The MR image reconstruction and transmission method of claim 1, wherein the plurality of artificial neural network models comprise:

a first neural network model, which is trained to reconstruct the received MR image by reducing noise included in the received MR image based on the correlation between sub-sampled MR images and fully-sampled MR images, when the protocol information corresponds to a first protocol;

a second neural network model, which is trained to reconstruct the received MR image by enhancing a resolution of the received MR image based on the correlation between sub-sampled MR images and fully-sampled MR images, when the protocol information corresponds to a second protocol; and a third neural network model, which is trained to reconstruct the received MR image by performing post-processing using 3D slice direction information based on the correlation between sub-sampled MR images and fully-sampled MR images, when the protocol information corresponds to a third protocol.

6. A MR image reconstruction and transmission system communicating with a picture archiving and communication system (PACS) through an encrypted wired network, the MR image reconstruction and transmission system configured to, receive MR image data including a plurality of k-space data obtained by sub-sampling through accelerated imaging and digital imaging and communications in medicine (DICOM) data generated based on the k-space data from the PACS, by a control server of the MR image reconstruction and transmission system, encrypt the MR image data and store the encrypted MR image data by the control server, reconstruct the received MR image data using an artificial neural network model trained to learn a correlation between sub-sampled MR images and fully-sampled MR images based on feature information of the MR image data by a reconstruction server of the MR image reconstruction and transmission system, and transmit the reconstructed MR image data on the basis of an address from which the MR image data is received to the PACS by the control server, wherein the MR image reconstruction and transmission system is further configured to, obtain metadata including personal information from the MR image data, and a plurality of image slices by slicing a 3D image included in the MR image data, and encrypt the plurality of image slices by shuffling the plurality of image slices and encrypt the metadata by performing pseudonymization by replacing personal identification information within the metadata, and wherein the MR image reconstruction and transmission system is further configured to, rearrange a spatial stacking order of the plurality of image slices with respect to at least one plane among a coronal plane, a sagittal plane, and an axial plane, which constitute the MR image data, and wherein the MR image reconstruction and transmission system is further configured to, decrypt the stored encrypted MR image data, transmit the decrypted MR image data to a manager server of the MR image reconstruction and transmission system by the control server when a request for the MR image reconstruction is received, identify protocol information and sequence information included in the feature information by the manager server and identify the artificial neural network model corresponding to the protocol information and the sequence information among a plurality of artificial neural network models by the manager server, wherein the protocol information and the sequence information being set in a MR device for the accelerated imaging, and reconstruct the received MR image data by inputting the received MR image data into the identified artificial neural network model by the reconstruction server, wherein the protocol information is information set in the MR device corresponding to an anatomical region and lesion to be imaged by the MR device, and wherein the sequence information is information comprising a combination of a plurality of sequences set in the MR device for the accelerated imaging, the combination defining the protocol information.

7. The MR image reconstruction and transmission system of claim 6, wherein the encrypted MR image data is stored, and unencrypted MR image data is deleted.

8. The MR image reconstruction and transmission system of claim 6, wherein the MR image data is classified according to feature information of the MR image data, and the MR image data classified according to the feature information is transmitted to the artificial neural network model so that the classified MR image data is input in a distributed manner to the plurality of artificial neural network models classified in advance on the basis of the feature information.

9. The MR image reconstruction and transmission system of claim 8, wherein, when the feature information includes both the protocol information and the sequence information, a protocol image set is generated from the MR image data on the basis of the protocol information, a plurality of MR images included in the protocol image set are classified into the sequence information, a sequence image set is generated on the basis of the classified sequence information, and a sequence set is transmitted to the artificial neural network model.

10. The MR image reconstruction and transmission system of claim 6, wherein the plurality of artificial neural network models comprise:

a first neural network model, which is trained to reconstruct the received MR image by reducing noise included in the received MR image based on the correlation between sub-sampled MR images and fully-sampled MR images, when the protocol information corresponds to a first protocol;

a second neural network model, which is trained to reconstruct the received MR image by enhancing a resolution of the received MR image based on the correlation between sub-sampled MR images and fully-sampled MR images, when the protocol information corresponds to a second protocol; and a third neural network model, which is trained to reconstruct the received MR image by performing post-processing using 3D slice direction information based on the correlation between sub-sampled MR images and fully-sampled MR images, when the protocol information corresponds to a third protocol.

* * * * *